(12) United States Patent
Samakar

(10) Patent No.: US 11,585,339 B2
(45) Date of Patent: Feb. 21, 2023

(54) JET PUMP FOR NONCONTACT TONOMETRY AND ASSOCIATED DEVICES, SYSTEMS, AND METHODS

(71) Applicant: Twenty Twenty Therapeutics LLC, South San Francisco, CA (US)

(72) Inventor: Amir Samakar, Fremont, CA (US)

(73) Assignee: Twenty Twenty Therapeutics LLC, South San Francisco, CA (US)

( * ) Notice: Subject to any disclaimer, the term of this patent is extended or adjusted under 35 U.S.C. 154(b) by 443 days.

(21) Appl. No.: 16/820,315

(22) Filed: Mar. 16, 2020

(65) Prior Publication Data
US 2020/0300236 A1    Sep. 24, 2020

Related U.S. Application Data

(60) Provisional application No. 62/819,907, filed on Mar. 18, 2019.

(51) Int. Cl.
| | | |
|---|---|---|
| *F04B 49/08* | (2006.01) | |
| *F04B 53/10* | (2006.01) | |
| *A61B 3/16* | (2006.01) | |

(52) U.S. Cl.
CPC .............. *F04B 49/08* (2013.01); *A61B 3/165* (2013.01); *F04B 53/1095* (2013.01)

(58) Field of Classification Search
CPC . A61B 3/16; A61B 3/165; F04B 49/22; F04B 49/08; F04B 53/1095
USPC ........................................................ 600/401
See application file for complete search history.

(56) References Cited

U.S. PATENT DOCUMENTS

| | | | |
|---|---|---|---|
| 3,232,099 A | | 2/1966 | Motchenbacher |
| 4,724,843 A | | 2/1988 | Fisher |
| 4,770,181 A | * | 9/1988 | Tomoda ................. A61B 3/165 600/401 |
| 5,048,526 A | * | 9/1991 | Tomoda ................. A61B 3/165 600/401 |
| 5,299,573 A | * | 4/1994 | Kobayashi ............. A61B 3/165 600/401 |
| 5,523,808 A | * | 6/1996 | Kohayakawa ........... A61B 3/18 600/401 |
| 5,639,224 A | * | 6/1997 | Schlossarczyk ........ F04B 49/08 417/306 |
| 5,779,633 A | * | 7/1998 | Luce ...................... A61B 3/165 600/401 |

(Continued)

FOREIGN PATENT DOCUMENTS

JP    H0716212 A  *  1/1995

*Primary Examiner* — Zachary W Wilkes
(74) *Attorney, Agent, or Firm* — Haynes and Boone, LLP

(57) ABSTRACT

Pumps for noncontact tonometry are provided. In one embodiment, a pump for noncontact tonometry includes a compression pump, a compression chamber, a first pressure sensor in communication with the compression chamber, a surge chamber, and a valve separating the compression chamber and surge chamber. The compression pump compresses a first volume of gas into the compression chamber. When the first pressure sensor detects a threshold pressure in the compression chamber, the valve opens and releases the gas into a surge chamber, where it combines with a gas residing in the surge chamber to form a puff of gas that escapes from the surge chamber through a flow-limiting nozzle. The components of the pump, which relies on passive rather than active components to create the controlled puff, can be assembled to have a profile that is portable and fit for home use.

20 Claims, 13 Drawing Sheets

(56) References Cited

U.S. PATENT DOCUMENTS

| | | | | |
|---|---|---|---|---|
| 5,947,898 A * | 9/1999 | Suzuki | | A61B 3/165 600/405 |
| 6,159,148 A * | 12/2000 | Luce | | A61B 3/165 600/405 |
| 6,361,495 B1 | 3/2002 | Grolman | | |
| 6,616,609 B2 * | 9/2003 | Siskowski | | A61B 3/165 600/401 |
| 6,623,429 B2 | 9/2003 | Percival et al. | | |
| 6,817,981 B2 | 11/2004 | Luce | | |
| 6,875,175 B2 * | 4/2005 | Luce | | A61B 3/165 600/398 |
| 8,652,044 B2 | 2/2014 | Abramov | | |
| 2002/0049373 A1 * | 4/2002 | Miwa | | A61B 3/165 600/401 |
| 2003/0088170 A1 * | 5/2003 | Siskowski | | A61B 3/165 600/401 |
| 2003/0088171 A1 * | 5/2003 | Siskowski | | A61B 3/165 600/401 |
| 2003/0092979 A1 * | 5/2003 | Luce | | A61B 3/165 600/398 |
| 2004/0046936 A1 | 3/2004 | Iwanaga | | |
| 2007/0055122 A1 | 3/2007 | Luce | | |
| 2008/0242966 A1 * | 10/2008 | Sagehashi | | A61B 3/165 600/401 |
| 2010/0030056 A1 | 2/2010 | Abramov | | |
| 2012/0190961 A1 | 7/2012 | Luce | | |
| 2013/0331679 A1 * | 12/2013 | Dobashi | | A61B 3/165 600/401 |
| 2014/0257076 A1 * | 9/2014 | Shimozato | | A61B 3/165 600/401 |

* cited by examiner

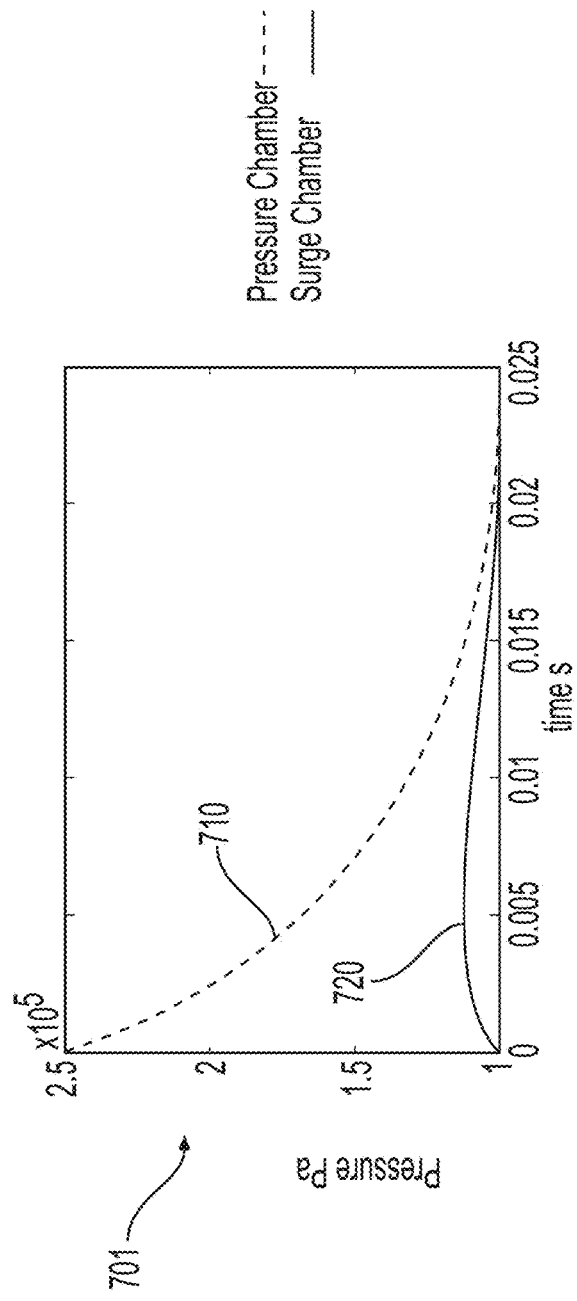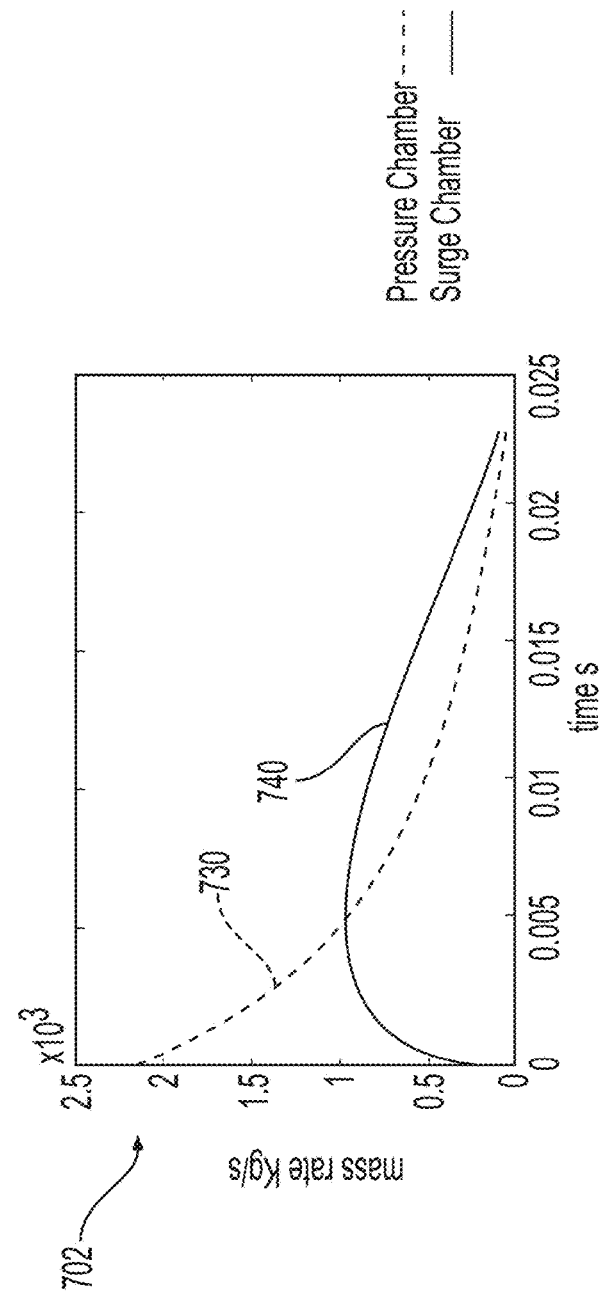
FIG. 6A
FIG. 6B

JET PUMP FOR NONCONTACT TONOMETRY AND ASSOCIATED DEVICES, SYSTEMS, AND METHODS

CROSS-REFERENCE TO RELATED APPLICATIONS

The present application claims priority to and the benefit of U.S. Provisional Patent Application No. 62/819,907, filed Mar. 18, 2019, the entirety of which is incorporated by reference.

TECHNICAL FIELD

The present disclosure relates generally to devices and methods for measuring intraocular pressure (IOP) in human eyes, and in particular to devices that generate a controlled air puff for noncontact tonometry.

BACKGROUND

Intraocular pressure (IOP) quantifies the pressure of the aqueous humor inside the eye. Many individuals suffer from disorders, such as glaucoma, that cause chronic heightened IOP. Over time, heightened IOP can cause damage to the optical nerve of the eye, leading to loss of vision. Effective treatment of glaucoma (e.g., using pharmaceutical agents) requires adherence to dosage schedules, and a knowledge of the patient's IOP. The more current or recent the measurement is, the more relevant it will be and hence the more effective the resulting treatment can be. The IOP for a given patient can vary significantly based on time of day, exercise, recency of medication use, and other factors. This means that any given measurement is subject to uncertainty, so it may take a plurality of measurements over time to provide confidence as to the health status of the patient. IOP measurements performed in a doctor's office typically only take place once or twice per year. These infrequent measurements are less capable to account for variation in patient IOP. Annual or biannual measurements in a doctor's office may also grow stale or obsolete due to time lag since the previous measurement. Frequent measurements at home could allow for better treatment at lower cost.

IOP may be measured through tonometry. It is to be appreciated that commonly used tonometry techniques and devices have numerous drawbacks. Contact tonometry is performed in a medical setting, and carries both an infection risk and a risk of injury. The procedure may also require numbing of the patient's eyes, resulting in both inconvenience and discomfort. Noncontact tonometry involves directing a puff or jet of air at the patient's eye and measuring the resulting deflection of the eye. However, the need to generate an air puff with a duration of about 20 milliseconds requires piston pumps with fast acceleration, which in turn requires a large solenoid, high coil force and high electrical power. This necessitates a relatively large device to accommodate the large coil, piston, power supply, and a printed circuit board (PCB) incorporating large capacitors. The solenoid and piston are metallic parts and are therefore relatively heavy. Accordingly, such pumps can be relatively expensive, as the piston pump requires accurate machining to minimize dry friction, and the control loop requires a fast embedded system and a precise acoustic pressure sensor. This large cost, weight, size, and power consumption make conventional noncontact tonometers impractical for home use. In addition, closed loop control of a piston to follow such a fast trajectory is possible only with limited accuracy. Accordingly, long-felt needs exist for air pumps that address the forgoing and other concerns.

SUMMARY

The present disclosure advantageously describes embodiments of a jet pump for noncontact tonometry. The jet pump is an air pump that employs a multi-chamber system to create a controlled puff or pulse of air with a desirable pressure profile for measuring the IOP of human eyes. The components of the jet pump, which relies on passive rather than active components to create the controlled puff, can be assembled to have a profile that is portable and fit for home use.

In one embodiment, a pump for noncontact tonometry includes a compression pump, a compression chamber in communication with the compression pump, a first pressure sensor in communication with the compression chamber, a surge chamber in communication with the compression chamber and configured to contain a gas, a flow-limiting nozzle in communication with the surge chamber, the flow-limiting nozzle comprising a throat having a throat diameter, and a valve separating the compression chamber and surge chamber, having both open and closed positions, and an aperture having an aperture diameter. The compression pump is configured to compress a first volume of gas into the compression chamber. The valve is configured to switch, in response to the first pressure sensor detecting a threshold pressure in the compression chamber, from the closed position to the open position such that the first volume of gas moves from the compression chamber to the surge chamber, and such that the first volume of gas combines with a gas residing in the surge chamber to form a puff of gas that escapes from the surge chamber through the flow-limiting nozzle.

In some embodiments, the pump further includes a controller configured to activate the compression pump, detect a threshold pressure within the compression chamber sensed by the first pressure sensor, deactivate the compression pump based on detecting the threshold pressure, and switch the valve from the closed position to the open position, based on detecting the threshold pressure. In some embodiments, the pump includes one or more batteries configured to supply electrical power to the compression pump, the first pressure sensor, and the valve. In some embodiments, the pump includes a second pressure sensor in communication with the surge chamber.

In one aspect, the flow-limiting nozzle is configured to form a puff with a rising pressure from a first time to a second time, a peak pressure occurring at the second time, and a falling pressure from the second time to a third time. In another aspect, a static pressure of the air stream is about 30 mmHg. In still another aspect, the second time is separated from the first time by an interval of between 5 milliseconds and 30 milliseconds. In one aspect, the third time is separated from the second time by an interval of between 4 milliseconds and 30 milliseconds. In a further aspect, the diameter of the aperture of the valve is between about 4 millimeters and about 6 millimeters, and the throat diameter of the flow-limiting nozzle is between about 2 millimeters and about 3 millimeters. In another aspect, a volume of the compression chamber is between 9 milliliters and 10 milliliters, and a volume of the surge chamber is between 20 milliliters and 30 milliliters.

In some embodiments, the compression chamber, surge chamber, and nozzle are arranged longitudinally to share a common axis. In another embodiment, the compression chamber is positioned longitudinally between the compression pump and the valve. In some embodiments, the puff of gas through the flow-limiting nozzle comprises a maximum volumetric flowrate determined based on the throat diameter of the flow-limiting nozzle.

In another embodiment of the present disclosure, a method of generating controlled gas puffs includes providing a compression chamber, a surge chamber, and a sonic nozzle, compressing a gas into the compression chamber until a threshold pressure value is reached, opening a valve to release the compressed gas through an aperture into the surge chamber, such that the compressed gas expands at a deterministic rate, and expelling the expanded gas from the surge chamber through a sonic nozzle such that the expanded gas escapes through the sonic nozzle forms a controlled puff with a rising pressure from a first time to a second time, a peak pressure occurring at the second time, and a falling pressure from the second time to a third time. The controlled puff can comprise a maximum volumetric flowrate determined based on a throat diameter of the sonic nozzle.

In some embodiments, the method includes directing the controlled puff at a cornea of an eye for noncontact tonometry, to determine an intraocular pressure of the eye. In some aspects, the second time is separated from the first time by an interval of between 5 milliseconds and 30 milliseconds, and the third time is separated from the second time by an interval of between 5 milliseconds and 30 milliseconds. In another aspect, expelling the expanded gas includes forming the controlled puff such that a static pressure of the controlled puff is about 30 mmHg.

In another embodiment of the present disclosure, a system for generating controlled air puffs for noncontact tonometry of a human eye includes a pump, a first container in communication with the pump, a first pressure sensor in communication with the first container, a second container in communication with the first container, a nozzle in communication with the surge chamber, the nozzle comprising a throat having a throat diameter, a valve separating the first container and the second container, and wherein the pump is configured to compress air into the first container until the first pressure sensor detects a threshold pressure, whereupon the valve is switched from a closed position to an open position to allow the air to move from the first container to the second container and escape from the second container through the nozzle.

In some embodiments, the system includes a housing configured such that the system can be readily held and supported by hand. The compression pump, the first container, the first pressure sensor, the second container, the nozzle, and the valve are coupled to the housing. In other aspects, the nozzle and second container are configured such that the air escapes from the second container with a maximum volumetric flow rate determined based on the throat diameter of the nozzle.

This summary is provided to introduce a selection of concepts in a simplified form that are further described below in the detailed description. This summary is not intended to identify key features or essential features of the claimed subject matter, nor is it intended to limit the scope of the claimed subject matter. A more extensive presentation of features, details, utilities, and advantages of the jet pump for noncontact tonometry, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIG. 6A is a graph depicting the pressure-vs.-time relationship for an example jet pump for noncontact tonometry in accordance with at least one embodiment of the present disclosure.

FIG. 6B is a graph depicting the flow rate-vs.-time relationship for an example jet pump for noncontact tonometry in accordance with at least one embodiment of the present disclosure.

DETAILED DESCRIPTION

Figure 1:
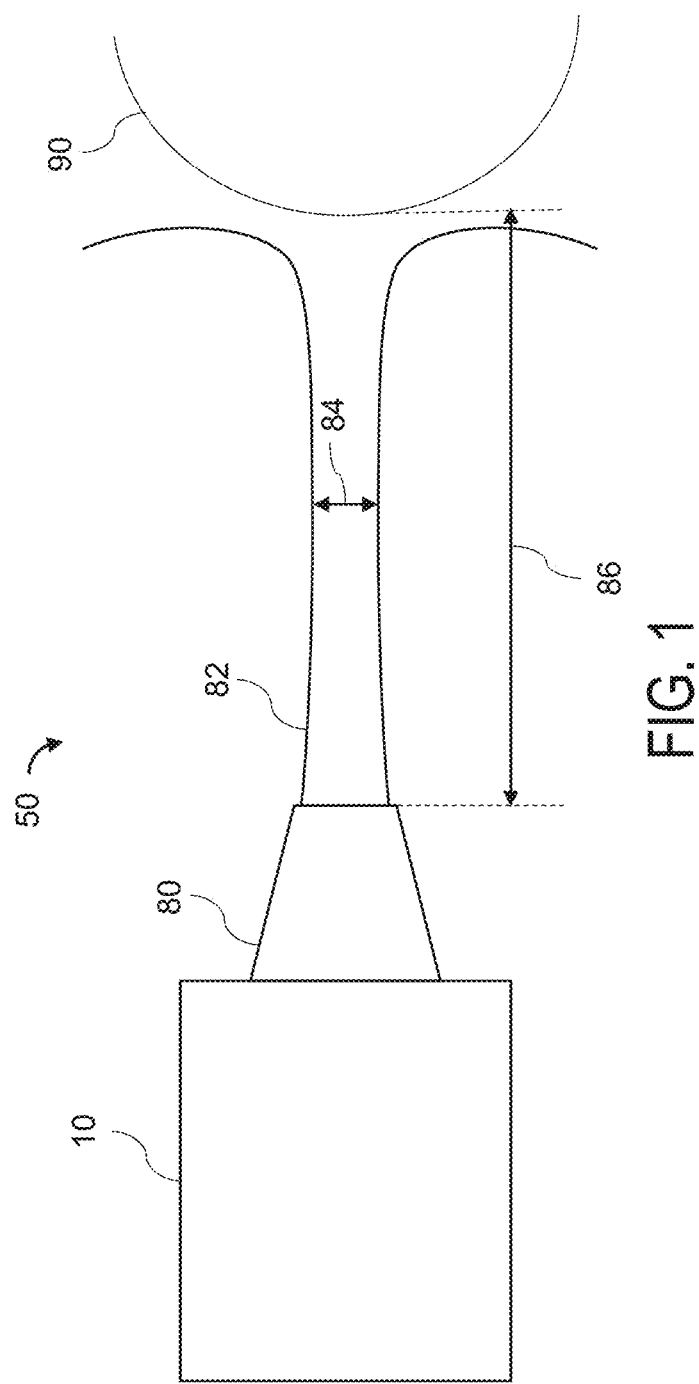
FIG. 1 is a diagrammatic view of a piston pump for noncontact tonometry in operation, according to the related art.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while devices of the present disclosure are described in terms of portable devices configured to direct air toward a human eye, it is understood that the disclosure is not intended to be limited to this application. The devices and systems are equally well suited to any application requiring pumping of brief puffs, pulses, or jets of air with certain profiles of pressure, density, and flow rate. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Presently, treatment of glaucoma mainly consists of periodically administering injections or eye drops to reduce IOP. However, the effectiveness of pharmaceuticals can greatly vary from patient-to-patient. Furthermore, the IOP for a given patient can vary significantly based on time of day, exercise, medication use, and other factors. This means that any given measurement is subject to considerable uncertainty, so it may take a plurality of measurements over time to provide confidence as to the health status of the patient and the proper dosage of medications. Effective treatment of glaucoma requires adherence to dosage schedules, and an accurate knowledge of the patient's IOP. The more recent the measurement is, the more it will reflect the patient's current condition, and thus the more effective the treatment will be. IOP measurements in a doctor's office, taking place once or twice per year, are unable to account for variation in patient IOP and measurements may grow stale due to time lag since the most recent measurement.

IOP may be measured through noncontact tonometry, which involves directing a puff of air at the patient's eye and measuring the resulting deflection. The air pressure required to temporarily flatten a region of the patient's cornea is equal to the patient's IOP. However, noncontact tonometry devices have traditionally employed piston pumps to generate the air puff. An exemplary noncontact tonometry device 50 for noncontact tonometry is shown in FIG. 1. The device 50 can include a pump 10 (e.g., a piston pump) that forces air through a nozzle 80, forming an output stream or air puff 82, which strikes a human eye 90. In an example, the distance between the nozzle 80 and the human eye 90 is between about 10 millimeters and 15 millimeters, although other values may be used. In an example, the diameter 84 of the output stream 82 is about 3 millimeters, although other values may be used. If the pump 10 is a piston pump, then the size, weight, power requirements, and closed-loop control circuitry of the piston pump 10 may make the piston pump 10 undesirable for portable and especially handheld or battery operated noncontact tonometers. The large cost, weight, size, and power consumption of the piston pumps used in these devices makes noncontact tonometry impractical for home use, and their low accuracy is believed to be the dominant driver in noncontact IOP measurement error.

The present disclosure advantageously describes jet pumps for noncontact tonometry, whose weight, size, power requirements, and cost make it appropriate for use for example in portable, handheld, perhaps battery operated noncontact tonometry devices. Features of the described jet pumps make them suitable for noncontact tonometers for use by a patient in the patient's home, potentially saving the patient visits to a clinician's office and providing the patient with the ability to take numerous IOP measurements. Features of the described jet pumps may provide for more accurate IOP measurements. According to some aspects, a jet pump for noncontact tonometry includes an air pump that employs a multi-chamber system to create a desirable pressure profile in the output air stream. A compression pump supplies air to a compression chamber, where a controller detects pressure using a pressure sensor. When the pressure exceeds a threshold value, a valve is opened, releasing the compressed air into a surge chamber, whose exit is a sonic nozzle that achieves choked flow, i.e., flow that restricts the maximum volumetric flowrate of the escaping air to a fixed value without wasting excessive amounts of energy.

The pressure exerted by the output air stream on the cornea increases over a brief period of time (in an example, 15 milliseconds), until it is sufficient to cause temporary applanation or flattening of the cornea, and then a brief period of slight concavity. The pressure then decreases over a period of time (e.g., 15 ms) such that the cornea flattens again before returning to its normal shape. In both moments of applanation, a noncontact tonometer detects the applanation with an optical sensor. The inner diameter of the throat of the sonic nozzle is approximately equal to the diameter of the region of the patient's cornea that will be temporarily flattened by the air jet, and the pressure within the surge chamber is approximately equal to the pressure exerted by the air jet on the patient's cornea, and hence also approximately equal to the patient's IOP at the moment of applanation.

In accordance with at least one embodiment of the present disclosure, a jet pump for noncontact tonometry is provided which creates an air stream with rising and falling pressure values appropriate for non-contact tonometry, and whose size, weight, and power requirements are consistent with a handheld noncontact tonometer for home use. The jet pump relies on a passive pneumatic circuit that does not require closed loop control; the pressure profile is a function of system geometry and initial pressure, while the flow rate is generated by a deterministic thermodynamic process. The energy is slowly stored in the compression chamber over a period of time (e.g., about 2 seconds, although other values may be used). Therefore, the compression pump may be relatively small and low-powered. The compression and surge chambers may be formed from inexpensive plastic, while the small pump and fast valve may be reliable, inexpensive off-the-shelf parts manufactured at high volumes. The disclosed jet pump is superior to conventional piston pumps for at least these reasons.

These descriptions are provided for exemplary purposes only and should not be considered to limit the scope of the disclosure. Certain features may be added, removed, or modified without departing from the spirit of the claimed subject matter.

Figure 2:
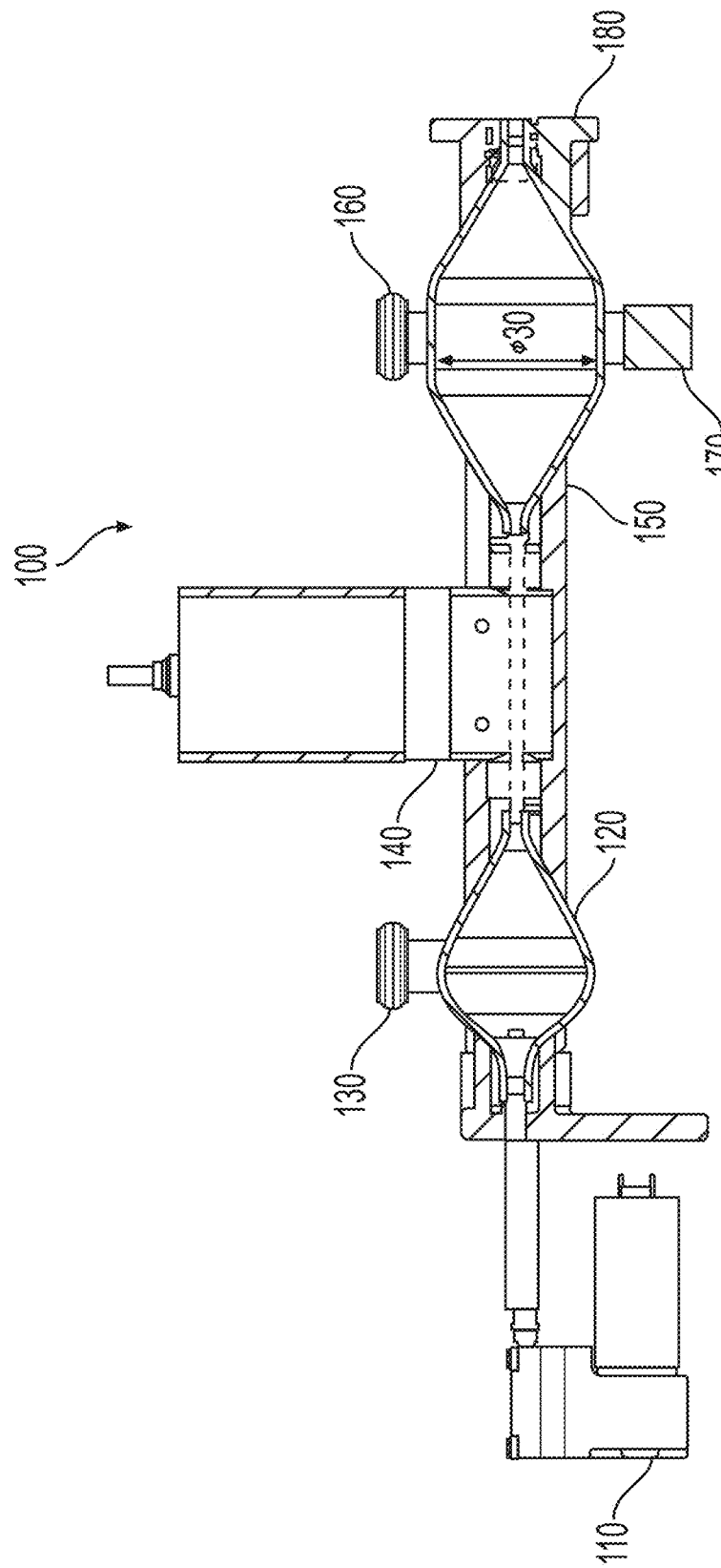
FIG. 2 is a diagrammatic view of an example jet pump for noncontact tonometry, according to at least one embodiment of the present disclosure.

FIG. 2 is a diagrammatic view of an example jet pump 100 appropriate for noncontact tonometry, according to at least one embodiment of the present disclosure. The jet pump 100 includes a compression pump 110, compression chamber 120, compression chamber pressure sensor 130, valve 140, surge chamber 150, and sonic nozzle 180. The jet pump may also include an optional surge chamber pressure sensor 160 or surge chamber acoustic pressure sensor 170. The compression pump 110 is an electrically operated air pump capable of pressurizing the compression chamber 120 to a specified pressure value over a specified period of time. In an example, the compression pump 110 is capable of pressurizing the compression chamber to 250 kPa (2.47 atmospheres) over a period of about 2.0 seconds. However, the compression pump may be capable of compressing air or gas in the compression chamber 120 to other specified pressure values, such as 150 kPa, 200 kPa, or any other suitable value. Further, the compression pump may be capable of compression the air or gas to the specified pressure value over different time periods, such as 1.0 seconds, 3.0 seconds, 5.0 seconds, 10 seconds, 15 seconds, or any other suitable amount of time. The compression pump 110 can include a solenoid piston pump weighing less than 300 grams. However, other types of pumps can be used, such as a rotary lobe, progressing cavity pump, rotary gear pump, screw pump, gear pump, vane pump, or any other suitable type of pump. In another example, a Parker CTS series coreless diaphragm pump is used, although other pumps may be used to achieve the same or a comparable effect.

The compression chamber 120 includes a pressure sensor 130. When the pressure within the compression chamber 120 exceeds a threshold value as measured by the pressure sensor 130, the high-speed valve 140 is opened, pneumatically connecting the compression chamber 120 to the surge chamber 150. The valve 140 may be controlled by and in communication with a processor or controller in communication with the pressure sensor 130. In an example, the compression chamber 120 is teardrop-shaped, has a volume of 10.6 ml, and releases its compressed air via the valve 140 at a deterministic profile of pressure and flowrate. In an example, the valve 140 has a switching time from the closed to the open state of between about 0.7 and about 1.0 milliseconds, with an error or uncertainty of about 15%. In an example, the valve 140 is an SMC SX12-DG fast solenoid valve or Festo Valve MHJ10-MF poppet valve, although other valves may also be used. In an example, the valve 140 has a pneumatic aperture diameter of 4 mm (0.157 inches) and supports a maximum flowrate of about 150 liters per minute, although other values may be used depending on the geometry of the compression chamber 120, surge chamber 150, and sonic nozzle 180.

Once the valve 140 has been opened, compressed air moves from the compression chamber 120, through the valve 140 and into the surge chamber 150. In an example, the surge chamber 150 has a volume of 26 milliliters, although other values may be used depending on the geometry of the compression chamber, valve, and sonic nozzle. For example, the volume of the surge chamber 150 can range from 10 ml to 100 ml. Further, the volume of the compression chamber 120 can range from 2 ml to 50 ml, in some embodiments. Compressed air that enters the surge chamber 150 expands at a deterministic rate, entraining the air already in the chamber to flow toward and exit through the sonic nozzle or critical flow sonic nozzle 180, which has a divergent-convergent nozzle shape. In an example, the sonic nozzle 180 has a throat with a diameter of 2.7 mm, and exactly achieves a choked flow with an average exit velocity of between about 80 m/s and 120 m/s, including values such as 100 m/s.

The compression pump 110 may optionally be switched off when the valve 140 is opened, both to conserve power and to reduce electrical noise and pressure fluctuations. In an example, including the compression pump 110 and controller 404 (FIGS. 6 and 7) required to operate it, the jet pump for noncontact tonometry weighs less than 90 grams. In an example, the peak power consumption of the jet pump for noncontact tonometry is about 4 Watts, an amount that can be supplied for example by two 12-Volt batteries delivering about 83 mA of current apiece, or by other common battery types. In the example shown, the compression pump 110, compression chamber 120, valve 140, and surge chamber 150 are all arranged along a central axis. However, in other examples these components may be placed side-by-side or in other configurations to minimize the size of the device or for other reasons.

Figure 3:
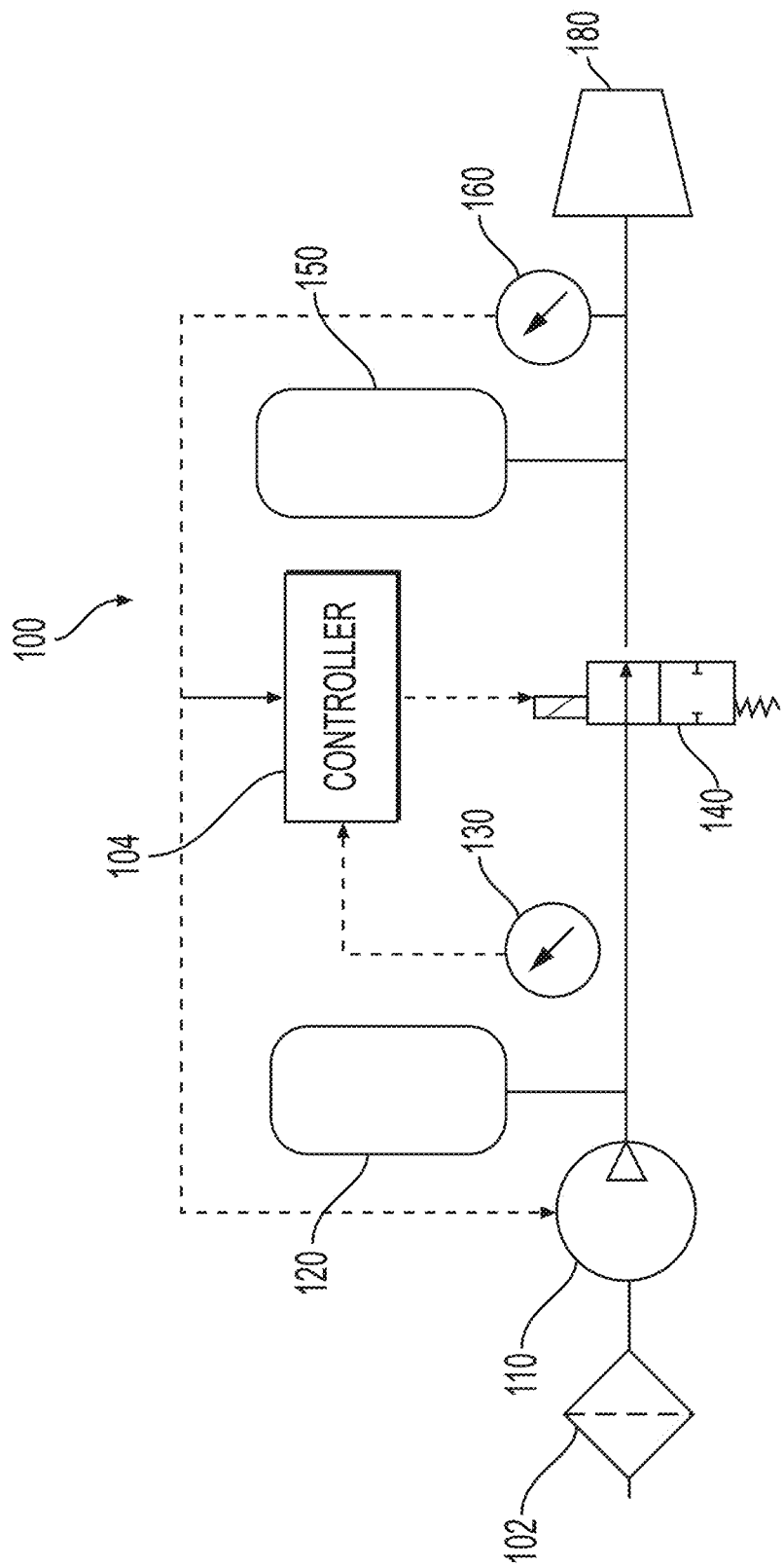
FIG. 3 is a schematic view of a pump for noncontact tonometry in operation, according to at least one embodiment of the present disclosure.

FIG. 3 is a schematic representation of an example jet pump for noncontact tonometry 100, according to at least one embodiment of the present disclosure. The embodiment of FIG. 3 also includes a filter 102 that prevents the pump 110 from aspirating particulates or other undesirable materials that might otherwise cause damage or discomfort to the eye if they were present in the output stream or air puff (not pictured). Further, the jet pump includes a controller 104, which is capable of receiving input values from pressure sensors 130 and 160, of switching on and off the pump 110 and the valve 140, and also of supplying power to the pump 110 and valve 140. In an example, the valve 140 is a normally closed valve. Furthermore, the noncontact tonometer can include a blink detection mechanism, such that the air puff is released immediately following a completed eye blink. For example, the blink detection mechanism may include a camera or optical sensor configured to detect when a patient has blinked. Once a blink is detected, the system triggers the pump to create a jet or puff of air immediately following the blink. If an air puff lasts 50 milliseconds or less, then the patient will generally not have time to blink again before an IOP measurement can be captured.

Figure 4:
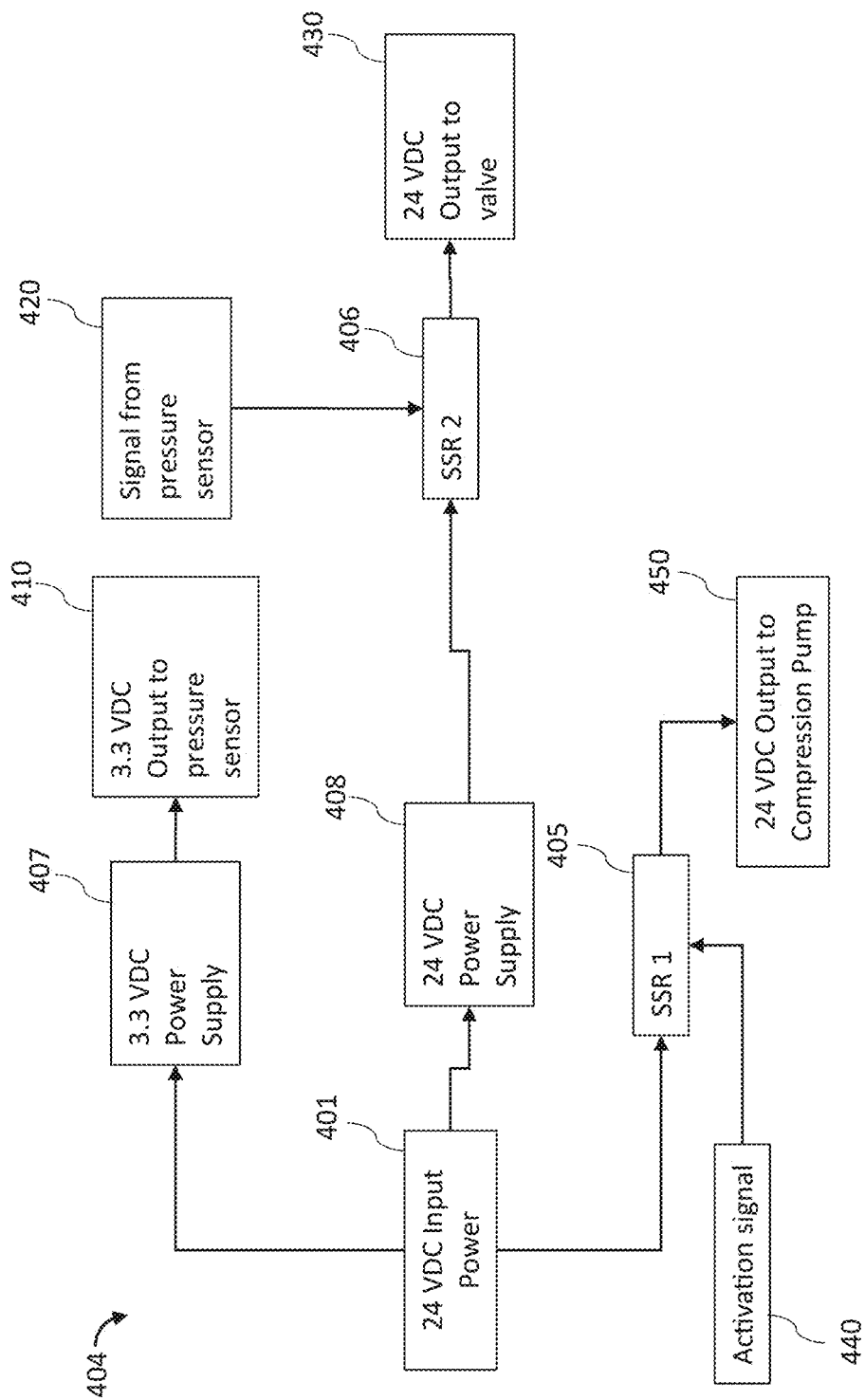
FIG. 4 is a functional block diagram of an example controller for a jet pump for noncontact tonometry, according to at least one embodiment of the present disclosure.

FIG. 4 is a functional block diagram of an example controller 404 for a jet pump for noncontact tonometry, according to at least one embodiment of the present disclosure. In an example, the controller 404 is configured to receive 24 Volt DC input power 401 from a battery or power supply (not pictured), such as two 12 VDC batteries connected in series. In an example, an external activation signal 440 (e.g., from an "on" switch external to the controller, or from a non-contact tonometer that includes the jet pump 100) is received by a first solid state relay (SSR 1) 405, which is configured to connect or disconnect the 24 VDC input power 410 and the compression pump 110 via a 24 VDC output 450. In an example, the 24 VDC input power 401 is also routed to a 3.3 VDC power supply 407 that supplies 3.3 VDC output power 410 to the pressure sensor 130. In an example, the 24 VDC input power 401 is additionally routed to a 5 VDC power supply 408.

In an example, the controller is configured to receive an input signal 420 from pressure sensor 130 (e.g., when a threshold pressure is reached), which signal is used to trigger the closure of a second solid state relay (SSR 2) 406 that, when closed, connects a 24 VDC power supply 408 to the valve 140 by producing a 24 VDC output 430, thus activating (i.e., opening) the valve 140. In some examples, the controller 404 is a breadboard, a printed circuit board, or an application specific integrated circuit (ASIC). A reader of ordinary skill in the art will understand that numerous different components and configurations could be provided within the controller to control the operation of the jet pump for noncontact tonomerty as described herein. In some embodiments, the controller may be a flex circuit, such that it may more readily be fitted into a compact housing along with the compression pump 110, compression chamber 120, valve 140, and surge chamber 150, along with other components such as wiring, sensors, and a battery, to create a jet pump 100 that is suitable for use with portable and especially handheld devices.

This arrangement of chambers, apertures, and nozzles produces a deterministic, passively regulated flow whose pressure-vs.-time and flowrate-vs.-time profiles are appropriate for noncontact tonometry, without the need for closed-loop control. As shown in FIG. 2, the surge chamber 150 may optionally include a pressure sensor 160 or acoustic pressure sensor 170. As the air puff (not pictured) impinges on the eye (not pictured), the pressure within the surge chamber 150 is approximately equal to the pressure applied to the cornea of the eye by the air puff, and the pressure within the surge chamber 150 at the moment of corneal applanation is approximately equal to the patient's IOP.

However, the pressure sensor 160 and acoustic pressure sensor 170 are optional, because the pressure within the surge chamber at any given time is deterministically known. Thus, in an example, a timer that is activated when the valve 140 is opened, coupled with a lookup table stored in a processor or memory location, either or both of which may be located on the controller or elsewhere, may serve the same function as either or both of the pressure sensor 160 and acoustic pressure sensor 170. In some embodiments, discrepancies between a pressure sensor 160 or 170 and a lookup table may be used to deduce the presence of leaks or other malfunctions within the jet pump 100.

Figure 5:
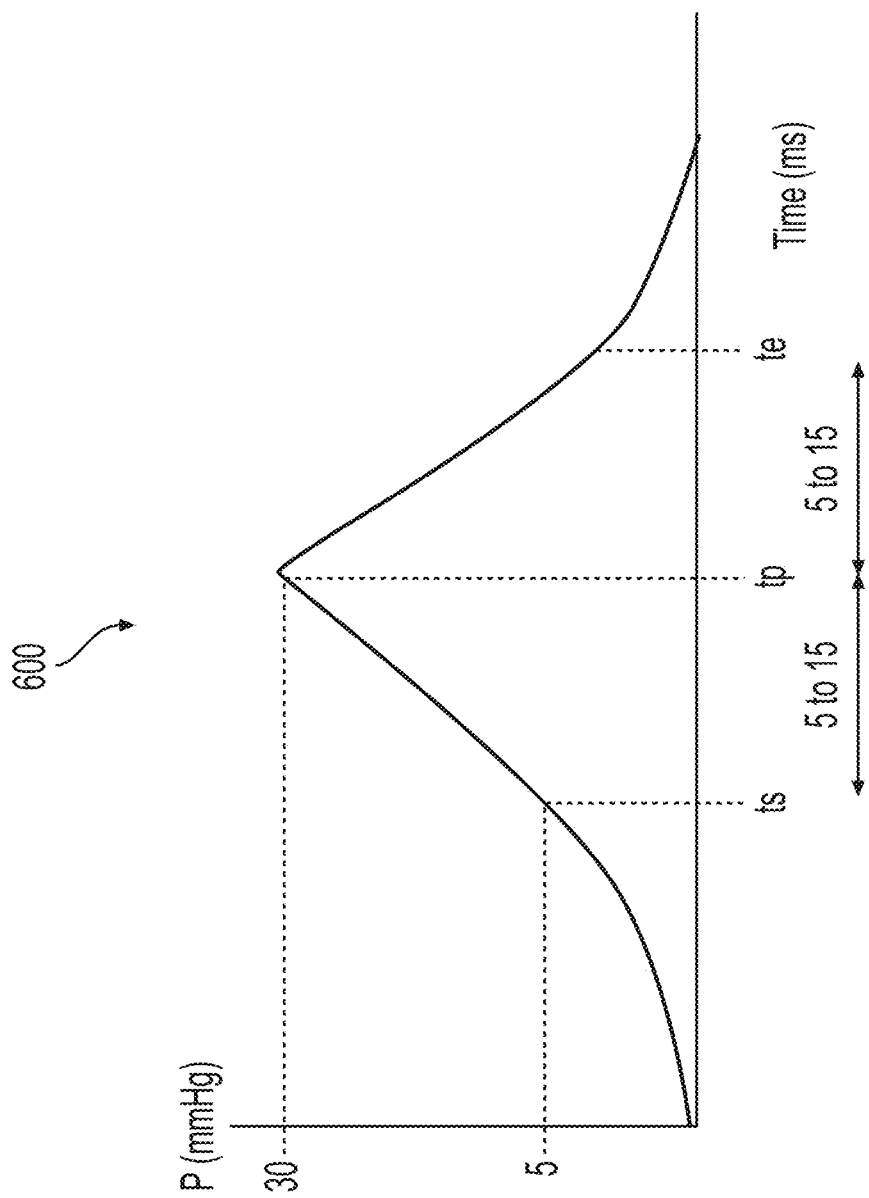
FIG. 5 is a graph depicting an exemplary idealized pressure-vs.-time curve for noncontact tonometry.

FIG. 5 is a graph 600 depicting an exemplary idealized pressure-vs.-time curve for noncontact tonometry. In an example, the desired maximum static pressure of the air puff on the center of the cornea is equal to about 30 mmHg (4.0 kPa or 0.04 atmospheres) above ambient pressure, with an accuracy of about ±1 mmHg. In an example, the startup time ts for the air puff is defined as the time when the pressure first reaches and exceeds 5 mmHg above ambient pressure, and the ending time te for the air puff is defined as the time when the pressure drops below 5 mmHg again, and the peak time tp is defined as the time when the pressure P reaches its maximum value. In an example, the pressure P rises from zero to 30 mmHg such that the rise time (i.e., tp minus ts) is between about 5 ms and about 15 ms in duration, and the fall time (i.e., te minus tp) is also between about 5 ms and about 15 ms in duration. Assuming the patient's IOP is somewhere between 5 mmHg and 30 mmHg, this will result in two separate applanation events—one during the rise time and one during the fall time. Any noncontact tonometer that reads these results will then have two separate IOP readings that may be reported separately, averaged, or otherwise.

As explained above, embodiments of the present disclosure contemplate the use of blink detection mechanisms in order to determine a preferred or optimal time to trigger the air puff. When the air puff has a duration of 5-50 milliseconds, the patient generally will not have time to blink before the puff is complete and the measurement or measurements have been taken. However, for air puffs of 50 milliseconds or longer, blinking during the measurement becomes a greater risk.

FIG. 6A is a graph 701 depicting the pressure-vs.-time relationship for an example jet pump for noncontact tonometry in accordance with at least one embodiment of the present disclosure. Unlike a piston pump, the compression pump 110 of the current disclosure provides a relatively low flowrate into the compression chamber 120 until a threshold overpressure is achieved, for example, over a period of two seconds. Once the threshold overpressure is achieved, the valve is opened. Thus, the pressure chamber pressure curve 710 shows its maximum value at t=0, i.e., the moment the valve is opened and the pump is optionally switched off. In an example, this maximum pressure is about 250 kPa (26.3 psi or 2.47 atmospheres). In an example, after t=0, the overpressure declines along a curve that is approximately asymptotic, such that at an elapsed time of t=25 ms the overpressure is approximately zero, meaning the air in the compression chamber 120 is approximately the same as the ambient pressure of the surrounding atmosphere.

Over this same time period, air enters the surge chamber 150 through the valve 140 and exits through the sonic nozzle 180 as described hereinabove, as shown in the surge chamber pressure curve 720. At t=0, the overpressure in the surge chamber 150 is equal to zero, because none of the compressed air from the compression chamber 120 has yet reached it through the valve 140. In an example, the overpressure rises over a period of about 5 ms, reaching the target pressure of 30 mmHg (0.039 atmospheres or 0.58 psi), and then declines to about zero at t=20 ms. This pressure curve 720 is consistent with the desired pressure profile for noncontact tonometry shown in FIG. 7, thus demonstrating that the jet pump 100 is appropriate for use in noncontact tonometry.

Figure 7:
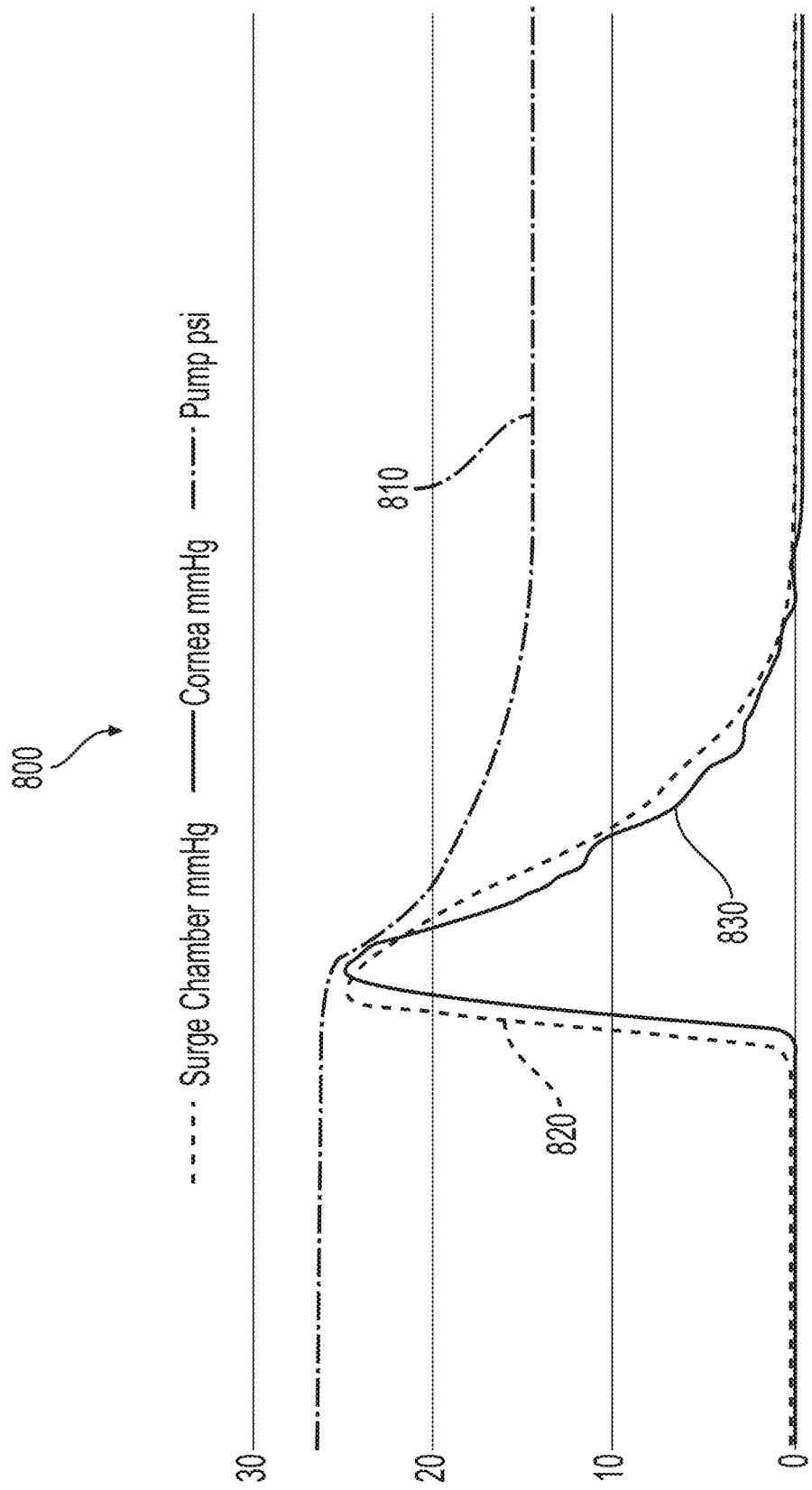
FIG. 7 is a graph depicting the pressure-vs.-time relationship for an example jet pump for noncontact tonometry in accordance with at least one embodiment of the present disclosure.
Figure 8:
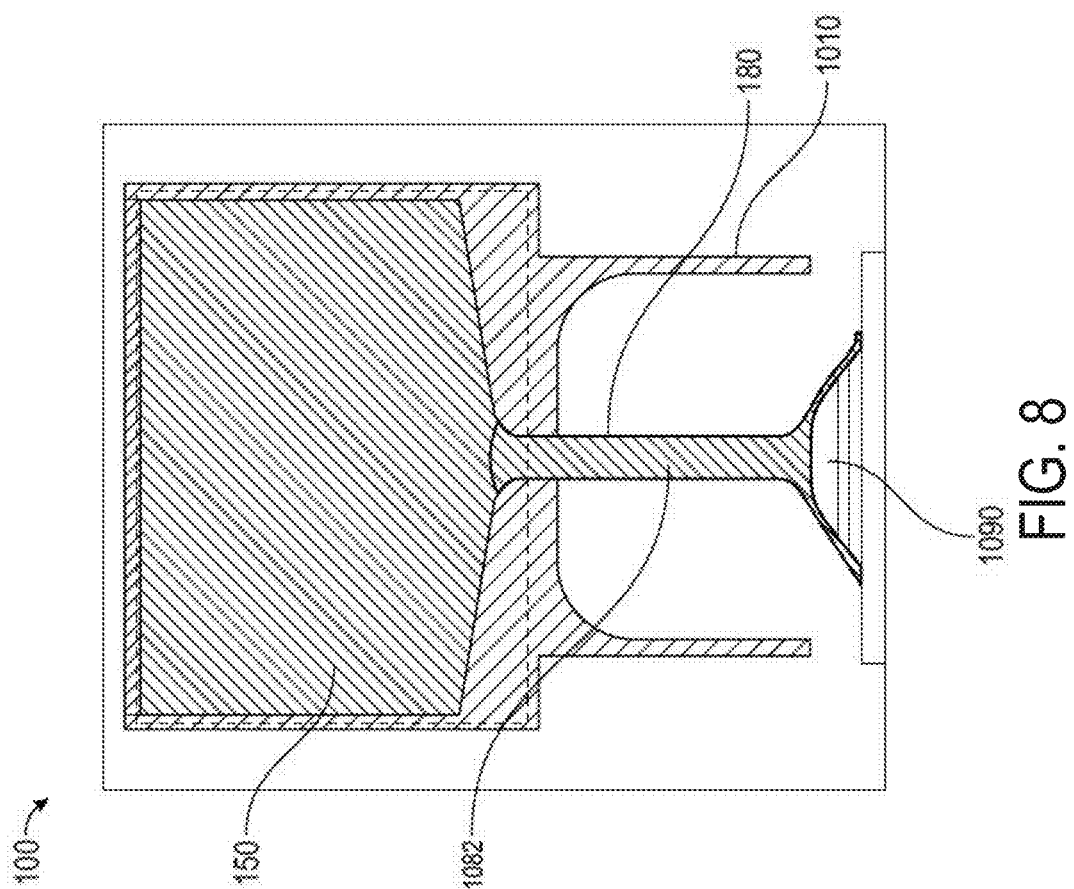
FIG. 8 is a diagrammatic view of a jet pump for noncontact tonometry in operation, according to at least one embodiment of the present disclosure.

It is to be noted with particular emphasis that without the surge chamber, a pressure profile of declining pressure, as with pressure curve 710, would be the only type of output stream the jet pump could produce, and without the sonic nozzle, the volumetric flowrate would not be limited to a fixed value, and therefore the pressure profile 720 of the surge chamber output stream would not exhibit a sharp peak as seen in FIGS. 8 and 7A. The surge chamber may also serve to suppress flow separation and therefore turbulence (vortex shedding) within the output stream.

FIG. 6B is a graph 702 depicting the mass flowrate-vs.-time relationship for an example jet pump for noncontact tonometry in accordance with at least one embodiment of the present disclosure. In an example, as with the pressure chamber pressure curve 710, the compression chamber flowrate curve 730 shows its largest value at t=0, and declines to approximately zero by approximately t=25 ms. In an example, the surge chamber flowrate curve 740 is zero at t=0, and peaks at about 1 kg/s at about t=5 ms, and declines to about zero at about t=25 ms.

FIG. 7 is a graph 800 depicting the pressure-vs.-time relationship for an example jet pump for noncontact tonometry in accordance with at least one embodiment of the present disclosure. As can be seen in the figure, the pressure 810 within the compression pump 110 remains at a high value until the valve 140 is opened, after which it declines over time to ambient pressure. Over the same time period, the surge chamber overpressure 820 begins at zero, rises to a peak value, and then declines to zero again. Because the sonic nozzle yields a precisely choked flow, there is little or no loss of pressure across the nozzle. Therefore, the overpressure 830 applied to the cornea closely tracks the surge chamber pressure, such that the two values may be considered equal for the purposes of noncontact tonometry.

FIG. 8 is a diagrammatic view of a jet pump for noncontact tonometry 100 in operation, according to at least one embodiment of the present disclosure. Visible are the surge chamber 150, sonic nozzle 180, output stream or air puff 1082, and eye or cornea 1090. Also visible is an optional skirt chamber 1010 which may be included as part of the jet pump for noncontact tonometry 100, or may be included as part of a noncontact tonometer that incorporates the jet pump for noncontact tonometry 100, or may be absent. The skirt chamber may, for example, rest against the user's cheekbones and forehead such that a proper distance between the sonic nozzle 180 and the eye 1090 is maintained.

In this example, the density of the output stream or air puff 1082 is only 3.2% different than the density inside the surge chamber 150, such that the two densities may be considered equal for purposes of noncontact tonometry.

Figure 9:
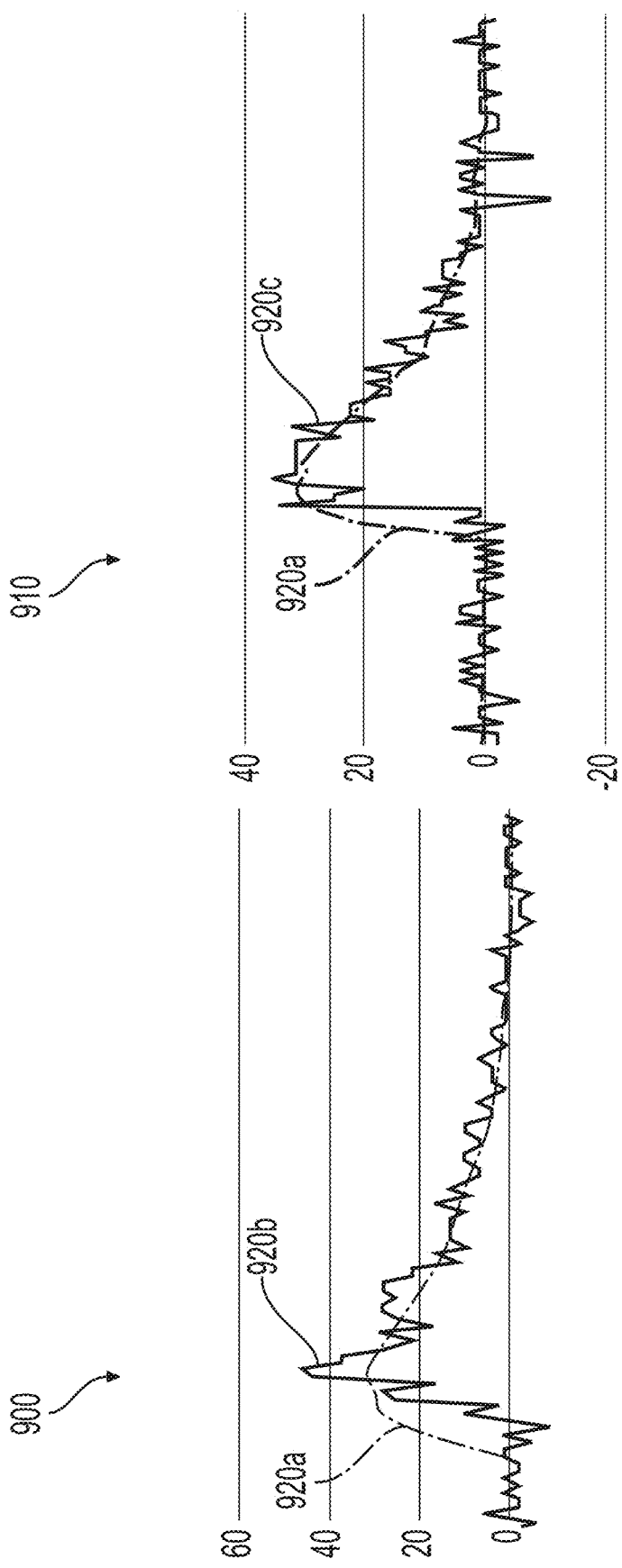
FIG. 9 is an exemplary graph depicting the pressure-vs.-time relationship for an exemplary jet pump for noncontact tonometry.

FIG. 9 is a graph depicting an exemplary pressure-vs.-time relationship 900 for an exemplary jet pump for noncontact tonometry. The graph 900 is divided into two parts for convenience, but shows three different pressure measurements vs. time for a single operation cycle of an exemplary jet pump 100. As can be seen in the graph 900, the surge chamber pressure curve 920a from a PCB-based sensor mounted inside the surge chamber 150 provides a relatively smooth rise and fall. Curves 920b and 920c are from remote pressure sensors separated from the surge chamber 150 by a 350 mm tube and a 115 mm tube, respectively. As a reader of ordinary skill will perceive from the graph, curves 920b and 920c provide signals that are substantially noisier than 920a, and also time-lagged by several milliseconds.

Figure 10:
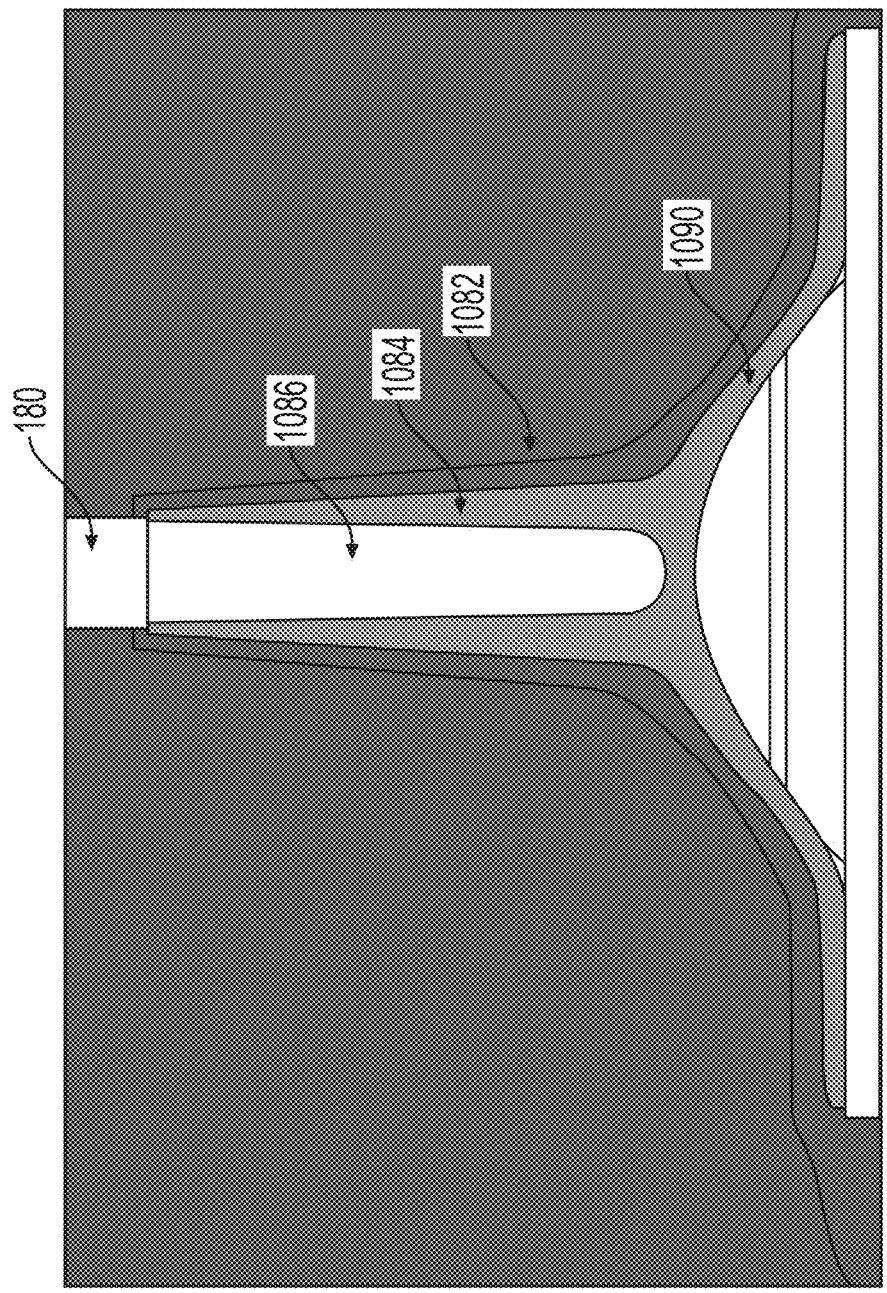
FIG. 10 is a diagrammatic view of a jet pump for noncontact tonometry in operation, according to at least one embodiment of the present disclosure.

FIG. 10 is a diagrammatic view of an example jet pump for noncontact tonometry 100 in operation, according to at least one embodiment of the present disclosure. The output stream or air puff 1082 leaves the sonic nozzle 180 and strikes the eye 1090. The width of the output stream 1082 increases slightly as the moving air travels from the sonic nozzle 180 to the eye 1090. However, the outer regions 1084 of the widened output stream 1082 are at lower velocity than the central regions 1086. The resulting region of substantially elevated pressure (45 kPa and higher) on the eye 1090 has a diameter similar enough to the inner diameter of the sonic nozzle 180 such that the two values may be treated as equal for purposes of noncontact tonometry. Preferably, if the distance between the cornea and the nozzle is smaller than 5 times the nozzle diameter, the energy loss in the air stream is negligible and the diameter of the elevated pressure region remains true to the nozzle diameter.

Depending on the implementation, the jet pump for noncontact tonometry may be made in different sizes, and with different sonic nozzle diameters defining different volumetric flowrates. The compression chamber, surge chamber, and sonic nozzle may be made from a variety of different materials including but not limited to metals and plastics, and may be fabricated with to a variety of different methods including but not limited to rolling, machining, injection molding, and 3D printing. Because it can be an open-loop pneumatic system that does not require large accelerated masses, high peak power, robust mechanics, or closed-loop controllers, the jet pump can be made smaller, more reliable, more affordable, and lighter than a comparable piston pump for noncontact tonometry. Accordingly, it can be seen that the jet pump for noncontact tonometry fills a long-standing need in the art, by providing an air pump that improves substantially on the drawbacks of piston pumps for delivering short, impulsive air puffs with a rising and falling pressure profile.

Figure 11:
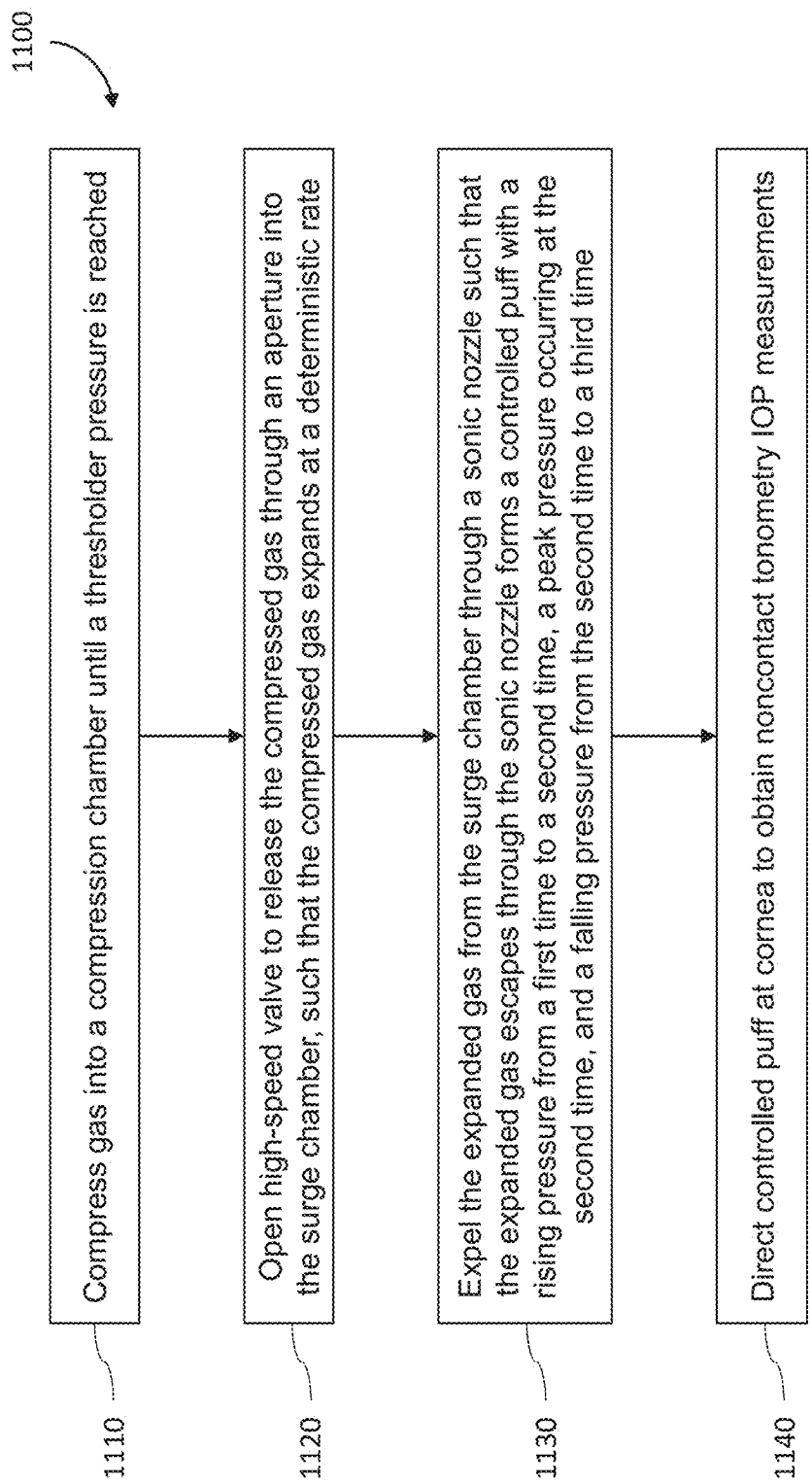
FIG. 11 is a flow chart illustrating a method for generating controlled gas puff, according to at least one embodiment of the present disclosure.

FIG. 11 is a flow chart illustrating a method 1100 for generating controlled gas puff, according to one embodiment. In some aspects, the method 1100 can be applied using a jet pump as described herein for noncontact tonometry to obtain IOP measurements of a patient's eye. In step 1110, a gas is compressed into a compression chamber of a jet pump for noncontact tonometry until a threshold pressure is reached. In step 1120, in response to the pressure of the compression chamber reaching the threshold pressure, a high-speed valve is opened to release the compressed gas through an aperture into a surge chamber, such that the compressed gas expands at a deterministic rate. In step 1130, the gas is expelled from the surge chamber through the throat of a sonic nozzle such that the expanded gas escapes through the sonic nozzle forms a controlled puff with a rising pressure from a first time to a second time, a peak pressure occurring at the second time, and a falling pressure from the second time to a third time. In step 1140, the controlled puff is directed at a cornea of a patient's eye to obtain IOP measurements.

Figure 12:
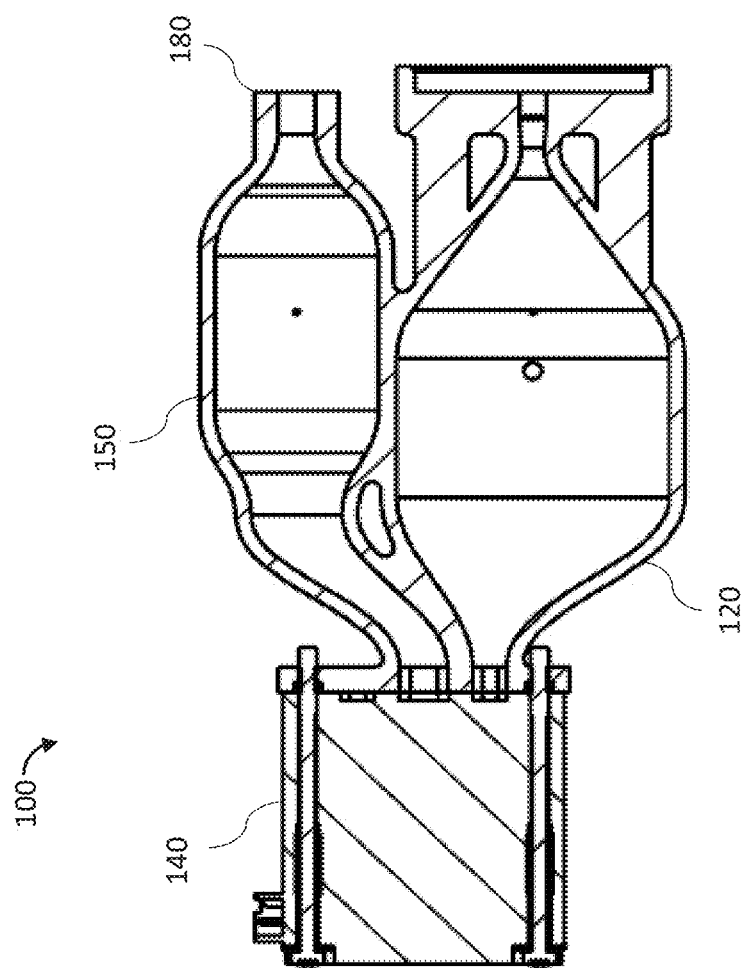
FIG. 12 is a cross-sectional view of a jet pump for noncontact tonometry in operation, according to at least one embodiment of the present disclosure.

As will be readily appreciated by those having ordinary skill in the art after becoming familiar with the teachings herein, the jet pump device could be configured in a variety of different ways. For example, as shown in the cross-sectional view of a non-contact tonometry device 100 in FIG. 12, the compression chamber 120 and surge chamber 150 could be located side-by-side and connected by a U-shaped connection rather than a straight tube, in order to create a more compact design. In other embodiments, the device 100 could include a mechanical control. For example, a pressure switch (capable of either or both of opening the valve 140 or shutting off the compression pump 110) serves as both the controller 104 and the compression chamber pressure sensor 130. The compression pump may be operated by some mechanism other than electricity, such as a spring or small internal combustion motor, or can be be operated manually. Alternatively, the device could be electrical, with an electrically operated pump, and a controller that comprises passive input lines, switches, and output lines that incorporate no memory or processing power. As still another alternative, the device could be electronically controlled, wherein the controller includes one or more clock, memory, logic, or processing devices. Logic or processing devices could be application specific or general purpose. The controller could employ any combination of hardware, software, and firmware to perform its functions. The controller could employ a fixed instruction set provided in read-only memory (ROM) or could have an updatable instruction set provided in programmable read-only memory (PROM), electrically erasable programmable read-only memory, flash memory, or any equivalent thereof. Readings taken from the pressure sensors 130, 160, and 160 may be stored on the device or communicated externally, as may the times the pump is activated, the times the valve is triggered, and/or a running tally of total times the device has been used. The pressure value required to trigger the valve may be adjustable or programmable, as may be the speed of the compression pump.

Figure 13:
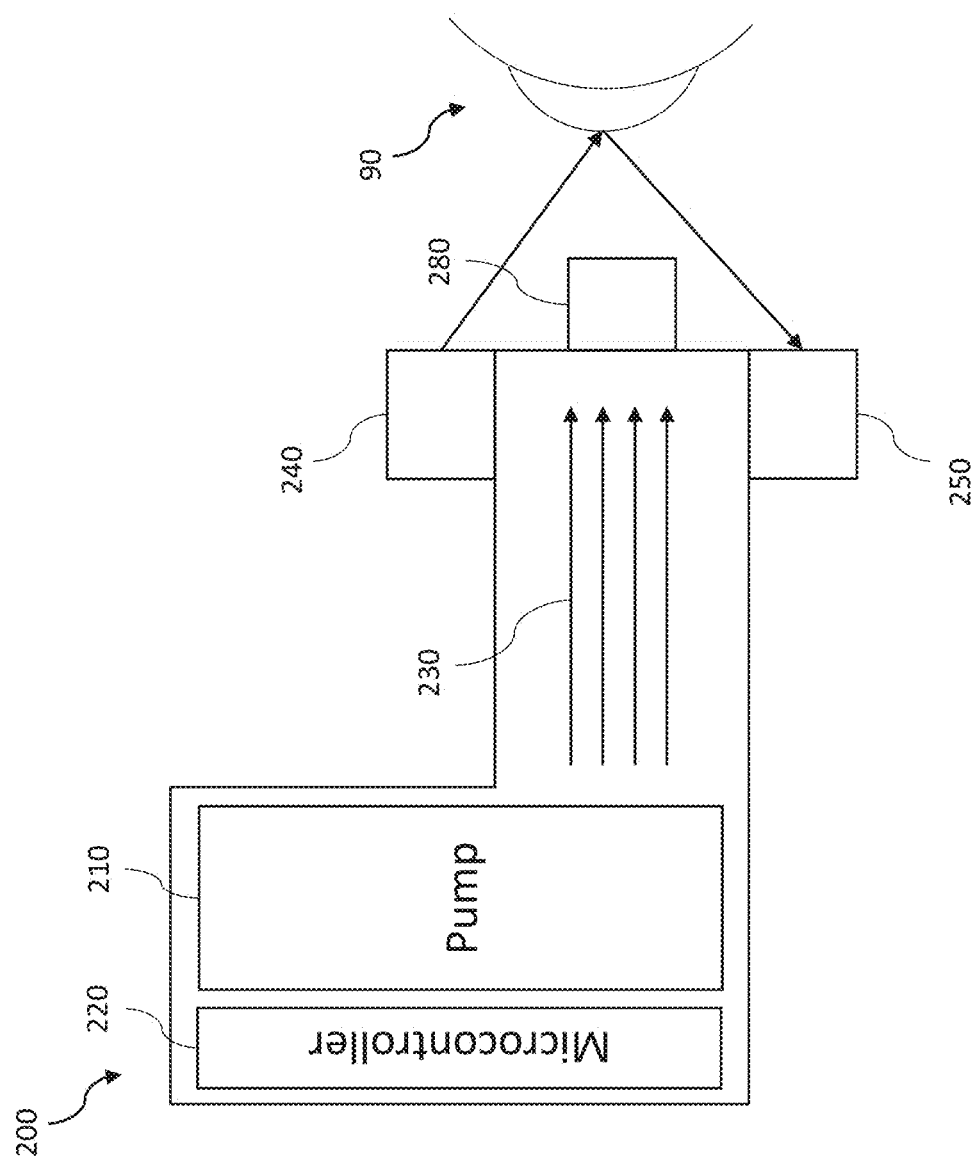
FIG. 13 is a diagrammatic schematic view of a noncontact tonometer, according to at least one embodiment of the present disclosure.

FIG. 13 illustrates a noncontact tonometer, or noncontact tonometry device 200 for performing IOP measurements at home. In that regard, the noncontact tonometer 200 shown in FIG. 15 may be portable, hand-held, or for desktop use. The noncontact tonometer 200 includes a pump 210, which may comprise the jet pump 100 described above, an optical source 240, an optical sensor or detector 250, and a nozzle 280 configured to direct a stream, jet, or puff 230 of gas to the patient's eye 90. The noncontact tonometer 200 also includes a microcontroller 220 configured to control one or more aspects of the pump 210, optical sensor or detector 250, and optical source 240. The optical source can include, for example, an InfraRed (IR) emitter, and the detector can be configured to detect IR signals. The microcontroller 220 may be configured to control a compression pump, pressure sensor, and/or valve of the pump 210 to generate and direct the jet or puff of gas 230 toward the eye 90, as described above. Further, the microcontroller 220 can be configured to activate a detection protocol following the generation of the puff of gas 230, whereby the optical source 240 emits an optical signal, and the optical detector 250 detects and/or measures the corresponding reflections of the optical signal. Based on the detected or measured reflections of the optical signal, the microcontroller 220 can determine or measure an amount of deflection of the eye 90, and determine IOP based on the measured deflection. Further, in come embodiments, the optical detector 250 comprises a camera configured to be controlled by the microcontroller for various steps in an IOP measurement protocol. For example, the camera can be used to identify and determine the position of the eye 90 relative to the nozzle 280 to ensure that the eye 90 is correctly positioned in the path of the puff of air 230. Further, the camera can be used for blink detection as described above.

Communication (including but not limited to software updates, firmware updates, or readings from the device) to and from the device 100 could be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. As explained herein, the disclosed pump devices may be included in a non-contact tonometer, such as in a hand-held non-contact tonometer. IOP measurements may be taken using the non-contact tonometer and communicated from the tonometer using the described wireless or wired communication capability.

A number of variations are possible on the examples and embodiments described above. For example, the shapes and relative sizes of the compression chamber and surge chamber could be altered, to change the shape of the pressure-vs-time curve shown for example in FIGS. 7A and 8, making it appropriate for other applications such as surface cleaning or drying, shooting "air balls" for recreational purposes, or otherwise.

The logical operations making up the embodiments of the technology described herein may be referred to variously as operations, steps, objects, elements, components, or modules. It should be understood that these may be performed or arranged in any order, unless explicitly claimed otherwise or a specific order is inherently necessitated by the claim language.

In some implementations, the compression pump may be an integral part of the jet pump. In other cases, it may be a separate component connected to the jet pump by, for example, an air hose. It should further be understood that the described technology may be employed as a standalone device or as a component of other devices.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the jet pump for noncontact tonometry. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the jet pump for noncontact tonometry as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. For example, the jet pump could be used to produce controlled puffs of other gases than ambient air, including but not limited to oxygen, nitrogen, helium, and argon, or of gases that contain colorants, odorants, medications, or other materials. Additionally, some or all of the components of the jet pump may be contained within a housing, either alone or with other components such as a battery and/or power supply.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims. Persons skilled in the art will recognize that the devices, systems, and methods described above can be modified in various ways not explicitly described or suggested above. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A pump for noncontact tonometry, comprising:
   a compression pump;
   a compression chamber in communication with the compression pump;
   a first pressure sensor in communication with the compression chamber;
   a surge chamber in communication with the compression chamber and configured to contain a gas;
   a flow-limiting nozzle in communication with the surge chamber, the flow-limiting nozzle comprising a throat having a throat diameter; and
   a valve separating the compression chamber and surge chamber, having both open and closed positions, and an aperture having an aperture diameter;
   wherein the compression pump is configured to compress a first volume of gas into the compression chamber, and wherein the valve is configured to switch, in response to the first pressure sensor detecting a threshold pressure in the compression chamber, from the closed position to the open position such that the first volume of gas moves from the compression chamber to the surge chamber, and such that the first volume of gas combines with a gas residing in the surge chamber to form a puff of gas that escapes from the surge chamber through the flow-limiting nozzle.

2. The pump of claim 1, further comprising a controller configured to:
   activate the compression pump;
   detect a threshold pressure within the compression chamber sensed by the first pressure sensor;
   deactivate the compression pump based on detecting the threshold pressure; and,
   switch the valve from the closed position to the open position, based on detecting the threshold pressure.

3. The pump of claim 1, further comprising one or more batteries configured to supply electrical power to the compression pump, the first pressure sensor, and the valve.

4. The pump of claim 1, further comprising a second pressure sensor in communication with the surge chamber.

5. The pump of claim 1, wherein the flow-limiting nozzle is configured to form a puff with a rising pressure from a first time to a second time, a peak pressure occurring at the second time, and a falling pressure from the second time to a third time.

6. The pump of claim 5, wherein a static pressure of the air stream is about 30 mmHg.

7. The pump of claim 5, wherein the second time is separated from the first time by an interval of between 5 milliseconds and 30 milliseconds.

8. The pump of claim 5, wherein the third time is separated from the second time by an interval of between 4 milliseconds and 30 milliseconds.

9. The pump of claim 5, wherein the diameter of the aperture of the valve is between about 4 millimeters and about 6 millimeters, and the throat diameter of the flow-limiting nozzle is between about 2 millimeters and about 3 millimeters.

10. The pump of claim 5, wherein a volume of the compression chamber is between 9 milliliters and 10 milliliters, and a volume of the surge chamber is between 20 milliliters and 30 milliliters.

11. The pump of claim 1, wherein the compression chamber, surge chamber, and nozzle are arranged longitudinally to share a common axis.

12. The pump of claim 1, wherein the compression chamber is positioned longitudinally between the compression pump and the valve.

13. The pump of claim 1, wherein the puff of gas through the flow-limiting nozzle comprises a maximum volumetric flowrate determined based on the throat diameter of the flow-limiting nozzle.

14. A method of generating controlled gas puffs, comprising:
providing a compression chamber, a surge chamber, and a sonic nozzle;
compressing a gas into the compression chamber until a threshold pressure value is reached;
opening a valve to release the compressed gas through an aperture into the surge chamber, such that the compressed gas expands at a deterministic rate; and
expelling the expanded gas from the surge chamber through a sonic nozzle such that the expanded gas escapes through the sonic nozzle forms a controlled puff with a rising pressure from a first time to a second time, a peak pressure occurring at the second time, and a falling pressure from the second time to a third time,
wherein the controlled puff comprises a maximum volumetric flowrate determined based on a throat diameter of the sonic nozzle.

15. The method of claim 14, further comprising directing the controlled puff at a cornea of an eye for noncontact tonometry, to determine an intraocular pressure of the eye.

16. The method of claim 15, wherein the second time is separated from the first time by an interval of between 5 milliseconds and 30 milliseconds; and,
wherein the third time is separated from the second time by an interval of between 5 milliseconds and 30 milliseconds.

17. The method of claim 15, wherein expelling the expanded gas comprises forming the controlled puff such that a static pressure of the controlled puff is about 30 mmHg.

18. A system for generating controlled air puffs for noncontact tonometry of a human eye, comprising:
a pump;
a first container in communication with the pump;
a first pressure sensor in communication with the first container;
a second container in communication with the first container;
a nozzle in communication with the second container, the nozzle comprising a throat having a throat diameter;
a valve separating the first container and the second container; and
wherein the pump is configured to compress air into the first container until the first pressure sensor detects a threshold pressure, whereupon the valve is switched from a closed position to an open position to allow the air to move from the first container to the second container and escape from the second container through the nozzle.

19. The system of claim 18, further comprising a housing configured such that the system can be readily held and supported by hand, wherein the compression pump, the first container, the first pressure sensor, the second container, the nozzle, and the valve are coupled to the housing.

20. The system of claim 18, wherein the nozzle and second container are configured such that the air escapes from the second container with a maximum volumetric flowrate determined based on the throat diameter of the nozzle.

* * * * *